United States Patent
Greiner et al.

(10) Patent No.: US 8,872,844 B2
(45) Date of Patent: Oct. 28, 2014

(54) METHOD OF DERIVING A GRAPHICAL REPRESENTATION OF DOMAIN-SPECIFIC DISPLAY OBJECTS ON AN EXTERNAL DISPLAY

(75) Inventors: Harald Greiner, Nufringen (DE); Uli Tessel, Ehningen (DE); Kai Hassing, Sindelfingen (DE)

(73) Assignee: Koninklijke Philips N.V., Eindhoven (NL)

( * ) Notice: Subject to any disclaimer, the term of this patent is extended or adjusted under 35 U.S.C. 154(b) by 1421 days.

(21) Appl. No.: 12/279,846

(22) PCT Filed: Feb. 9, 2007

(86) PCT No.: PCT/IB2007/050426
§ 371 (c)(1),
(2), (4) Date: Aug. 19, 2008

(87) PCT Pub. No.: WO2007/096802
PCT Pub. Date: Aug. 30, 2007

(65) Prior Publication Data
US 2009/0043175 A1    Feb. 12, 2009

(30) Foreign Application Priority Data
Feb. 20, 2006 (EP) .................................. 06110135

(51) Int. Cl.
*G09G 5/00* (2006.01)
*G06T 11/20* (2006.01)
*A61B 5/00* (2006.01)
*G06F 19/00* (2011.01)

(52) U.S. Cl.
CPC .......... *A61B 5/0013* (2013.01); *G06F 19/3406* (2013.01); *G06F 19/3418* (2013.01)

USPC ............................ 345/619; 345/440; 600/300

(58) Field of Classification Search
None
See application file for complete search history.

(56) References Cited

U.S. PATENT DOCUMENTS

| | | | |
|---|---|---|---|
| 5,038,800 A * | 8/1991 | Oba | 600/509 |
| 5,746,203 A * | 5/1998 | Hood, Jr. | 600/300 |
| 6,219,836 B1 * | 4/2001 | Wells et al. | 717/178 |
| 6,222,558 B1 | 4/2001 | Berg | |
| 6,406,426 B1 * | 6/2002 | Reuss et al. | 600/300 |
| 2001/0037366 A1 | 11/2001 | Webb et al. | |
| 2002/0054044 A1 | 5/2002 | Lu et al. | |
| 2003/0065717 A1 * | 4/2003 | Saito et al. | 709/203 |
| 2004/0044283 A1 * | 3/2004 | Yoneyama | 600/437 |
| 2005/0149001 A1 | 7/2005 | Uchikubo et al. | |
| 2006/0012612 A1 | 1/2006 | Johnston et al. | |

FOREIGN PATENT DOCUMENTS

| | | |
|---|---|---|
| EP | 1051945 A2 | 11/2000 |
| JP | H04108432 A | 4/1992 |
| JP | 2000194836 A | 7/2000 |
| JP | 2002244987 A | 8/2002 |
| WO | 03104966 A2 | 12/2003 |

* cited by examiner

*Primary Examiner* — Kee M Tung
*Assistant Examiner* — Frank Chen

(57) ABSTRACT

Technique for deriving a graphical representation of domain-specific display-objects on an external display (13) within a patient-monitoring system (1), in which only a small amount of data has to be transmitted to the external display device (3) and at the same time the user of the external display (13) gets the same "look and feel" as he is used to from the built-in display (12) of a patient monitor (2).

16 Claims, 1 Drawing Sheet

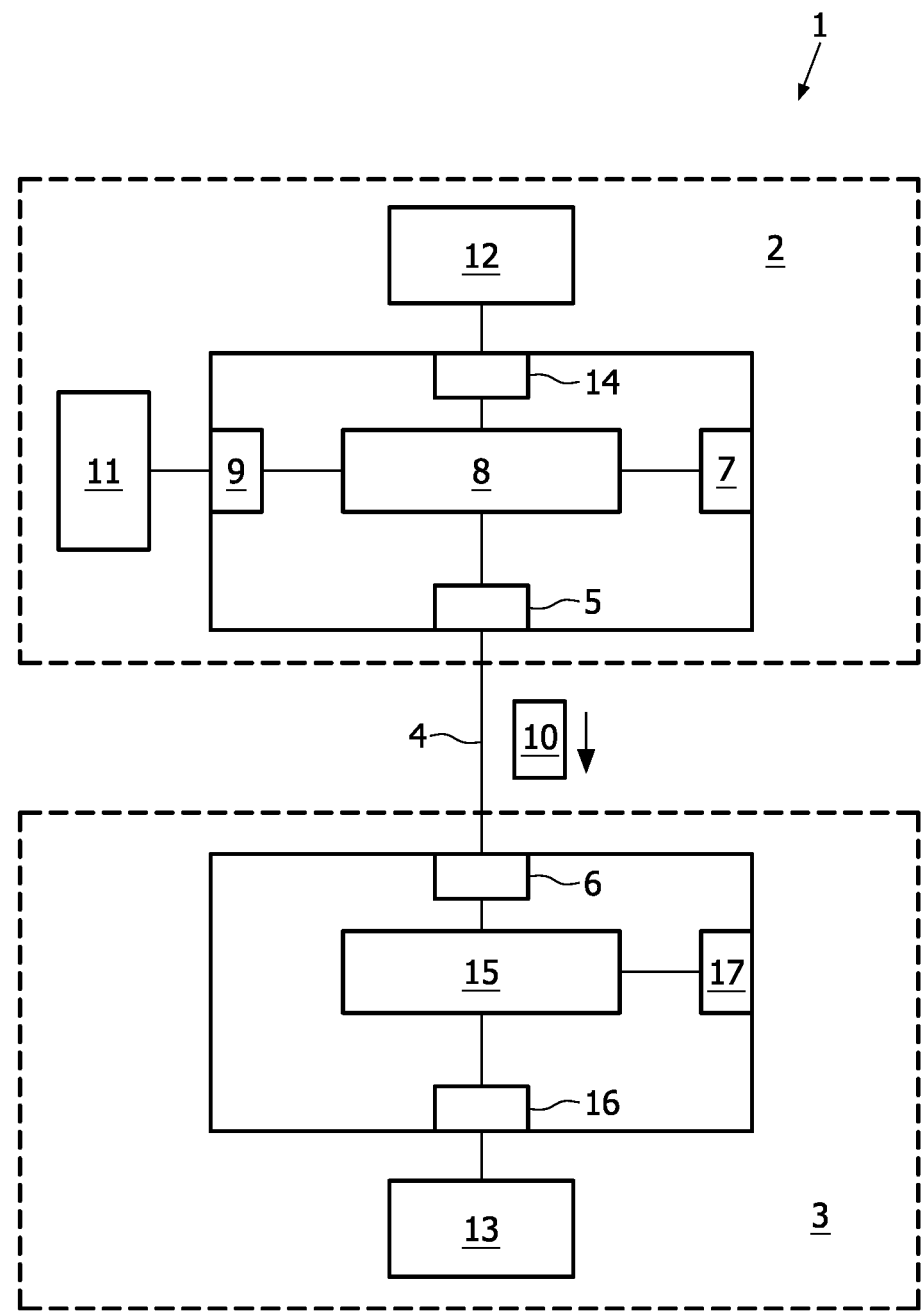

METHOD OF DERIVING A GRAPHICAL REPRESENTATION OF DOMAIN-SPECIFIC DISPLAY OBJECTS ON AN EXTERNAL DISPLAY

The present invention relates to a method of deriving a graphical representation of domain-specific display objects on an external display within a patient-monitoring system. Furthermore, the present invention relates to a patient-monitoring system and to computer programs for display management in such a patient-monitoring system.

Patient monitors are used in a medical environment for monitoring the patient's heart function, respiration, etc. Sometimes the built-in display of a patient monitor is not large enough for displaying all the information required by a physician or nurse. In such cases a second, external display may be connected to the patient monitor.

Two different approaches are known for controlling such an external. First, a remote graphical interface approach can be used. In this case the complete graphical data and user input is transferred to the external display. Examples of this approach are the UNIX-based "X-Windows" or the MICROSOFT concept of "Remote Desktop". These systems provide the same experience to a remote user as to a local user. A disadvantage of this approach is the large amount of data to be transmitted to the external display. Different kinds of optimization are employed, making this technique expensive, e.g. data compression, encoding of graphical primitives to be executed, and caching of data at the remote location. A second approach, instead of transmitting the whole data set, exports only raw data, and a complete second user interface is used in the remote location. Said second interface processes the raw data so as to generate the imaging information to be displayed on the external display. The data presentation and user interface on the external display are implemented independently of that of the sourcing patient monitor. A disadvantage of this approach is that the control of monitor functions (e.g. alarm limits) and the selection of various screen layouts are different from what the user is used to.

It is an object of the present invention to provide a technique for deriving a graphical representation of domain-specific display objects on an external display within a patient-monitoring system, in which only a small amount of data has to be transmitted to the external display and in which the user of the external display gets the same "look and feel" as he is used to from the built-in display of a patient monitor.

This object is achieved according to the invention by a method of deriving a graphical representation of domain-specific display objects on an external display within a patient-monitoring system, comprising the steps of processing monitoring data and generating communication data from the monitoring data by means of a first display management device, which is comprised in a patient monitor, wherein the communication data exclusively comprise logical data necessary for deriving a graphical representation of domain-specific display objects on the external display, transmitting the generated communication data to an external display device, which is connectable to the patient monitor, via a communication link, processing the transmitted communication data, generating imaging information from the communication data by means of a second display management device which is comprised in the external display device, and deriving a graphical representation of domain-specific display objects on the external display from the generated imaging information.

The object of the present invention is also achieved by a patient-monitoring system, comprising a patient monitor, which patient monitor comprises a first display management device adapted to process monitoring data and further adapted to generate communication data from the monitoring data, wherein the communication data exclusively comprises logical data necessary for deriving a graphical representation of domain-specific display objects on the external display, and further comprising an external display device, connectable to the patient monitor via a communication link adapted to transmit the communication data. which The external display device comprises a second display management device adapted to process the transmitted communication data and further adapted to generate imaging information from the communication data so as to derive a graphical representation of domain-specific display objects on the external display from the generated imaging information.

The object of the present invention is also achieved by a computer program for display management in a patient monitor of a patient-monitoring system, to be executed in a computer of the patient monitor, said program comprising computer instructions to process monitoring data and to generate communication data from the monitoring data, the communication data exclusively comprising logical data necessary for deriving a graphical representation of domain-specific display objects on an external display, when the computer program is executed in the computer.

The object of the present invention is also achieved by a computer program for display management in an external display of a patient-monitoring system, to be executed in a computer of an external display device, said program comprising computer instructions to process communication data and to generate imaging information from the communication data, and computer instructions to derive a graphical representation of domain-specific display objects on the external display from the generated imaging information, when the computer program is executed in the computer.

The technical effects necessary according to the invention can thus be realized on the basis of the instructions of said computer programs in accordance with the invention. Such computer programs may be stored on a carrier such as a CD-ROM or may be available over the internet or some other computer network. Prior to execution, the computer programs are read from the carrier and loaded into the computer, for example by means of a CD-ROM player, or from the internet, and stored in the memory of the computer. The computer includes inter alia a central processor unit (CPU), a bus system, memory means, e.g. RAM or ROM, etc., storage means, e.g. floppy disk or hard disk units, etc., and input/output units. Alternatively, the inventive method may be implemented in hardware, e.g. using one or more integrated circuits. In other words, the functionality of the present invention can be implemented in the form of hardware, software, or a combination of these two.

A display manager software serving as a first display management device is executed in a patient monitor according to the present invention. This display manager software is adapted for controlling the built-in display of the patient monitor. For this purpose the display manager software employs a special communication protocol which is neither graphical (as X-Windows) nor purely data-oriented. Instead, the communication is optimized to interface domain-specific display objects, as disclosed in the international patent application WO03/104966, which is incorporated herein by reference in its entirety. The display manager software processes a high-level communication protocol to derive a graphical representation on a display and to process user input actions (mouse movements, touch screen actions, etc.).

A core idea of the invention is to re-use the display manager software of the patient monitor (either in part or as a whole) in a different processing device, the "external display". Such a different processing device may be, for example, an identical platform, i.e. another patient monitor, or a different platform, e.g. a personal computer, a notebook, or some other type of general purpose computer, irrespective of processor type, operating system, environment, etc. Re-using the display manager software in said different processing device renders it possible to maintain the same communication as used "internally" in the patient monitor itself. Thus, the communication between the sourcing patient monitor and the external display is provided in a way such that a minimum amount of data has to be transmitted.

The communication protocol serves to exchange information between the patient monitor and the external display on display objects that do exhibit domain-specific behavior. The same object may be rendered totally differently, leading to different graphical representations on the external display and on the sourcing patient monitor.

According to the invention, neither raw data nor a complete graphic data set is transmitted from the patient monitor to the external display. Instead, the invention suggests to transmit exclusively logical data necessary for deriving the graphical representation of domain-specific display objects on the external display. Thus, the amount of transmitted data is small compared with the X-Windows approach. On the other hand, the user of the external display obtains all functions and screen layouts as though the built-in display of the patient monitor were used. In the external display, the transmitted data is used to generate the imaging information according to the domain specific behavior of the object to be displayed.

According to the invention, the graphical presentation is driven by a display manager software serving as a second display management device which is executed in the processing device of the external display. The functionality and behavior of the graphical representation is fully defined by (and therefore identical to) the implementation in the patient monitor.

The inventive method is easy to implement and to maintain, since it requires for the external display exactly the same functionality (display manager) that is already available on the patient monitor. Should the external display use a different hardware or software technology, it is only the rather small part of the rendering engine that needs to be exported, not the full functionality of a patient monitor.

Most of the algorithms to implement the domain-specific behavior can be implemented in a platform-independent manner. Usually only the basic graphic rendering engine which is dependent on the underlying video hardware, operating system, or basic graphical software interface needs to be re-implemented.

The external display according to the present invention guarantees a functional/behavioral consistency with respect to the patient monitor. At the same time the graphical presentation is very flexible. Since only changes in state or data need to be communicated between the patient monitor and the external display, there are lower bandwidth requirements than in the prior art solutions. There is no periodical communication if monitoring data (measurement data) does not change. No update of complete graphical data is necessary; thus extensive and complex algorithms for compression and caching are not needed. Optionally, however, graphical support data required or requested by the drawing algorithm to render a somewhat similar graphical presentation (e.g. labels, grid lines, color) may be sent periodically or on request. The hardware requirements of patient monitor and external display are comparatively low, since only data that will actually be displayed needs processing, and no rendering and compression of the complete graphical presentation are required.

These and other aspects of the invention will be described in detail hereinafter by way of example with reference to the following embodiments and the accompanying drawing of FIG. 1; which schematically illustrates a patient-monitoring system.

The patient-monitoring system 1 according to the invention comprises a patient monitor 2 and an external display device 3 that can be connected to the patient monitor 2 via a LAN communication link 4. For this purpose, the patient monitor 2 comprises a LAN compatible system interface 5, and the external display device 3 comprises a LAN interface 6. All components of the patient monitor 2 are connected to a power supply 7.

The patient monitor 2 comprises a processing unit (CPU) 8, in which a display manager software is executed; thus the CPU 8 serves as first display management device. The CPU 8 is adapted to process monitoring data (measurement data) by means of the display manager software, which data is transmitted from a sensor 9 via a measurement interface 11 of the patient monitor 2 to the CPU 8. The CPU 8 is further adapted to generate communication data 10 from the monitoring data by means of the display manager software. The methods as disclosed in the international patent application WO03/104966 are used for generating the communication data 10, i.e. an optimized presentation on a display screen of objects of a user interface is obtained, wherein the objects can be freely positioned and scaled by means of control elements. This is realized by means of a predetermined calculation rule such that the objects can be automatically varied between a still readable minimum size and a selected maximum size in dependence on the object contents, selected preferred settings, and the available display resource on the display screen, and such that the available display screen surface is optimally filled, possibly while eliminating less important details of the object contents and while changing the display mode of the object contents and/or the object as well as avoiding mutual overlapping of the objects.

For example, the CPU 8 generates layout information according to WO03/104966 for the objects to be displayed on a built-in display 12 and on a display 13 of the external display device 3. Such layout information comprises e.g. information on whether or not an object (e.g. a heart rate) is displayed as a digit or in the form of a graph. The layout information also comprises e.g. information about the size with which the object is to be displayed on the built-in display 12 and/or on the external display 13 of the external display device 3. For example, if the external display 13 has a larger display area than the built-in display 12 of the patient monitor 2, the layout information regarding the external display 13 may be arranged such that certain objects, e.g. objects relating to the lung functions of a patient, are always displayed in (large) graphical form on the external display 13, whereas other objects, e.g. objects of less importance, are always displayed in the form of (small) digits on the external display 13.

All of this layout information is combined with the object data of those objects that are to be displayed. As a result, the communication data 10 exclusively comprises logical data necessary for deriving a graphical representation of domain specific display objects on the external display 13. The communication data 10 does not comprise information about "how" the medical objects (e.g. heart rate) are displayed on the external display 13. Instead, the communication data 10 comprises information about the layout of these objects, e.g. their display size and arrangement.

The communication data 10 is transmitted via the LAN communication link 4 to the external display device 3 and will be further processed there. Other communication data intended for controlling the built-in display 12 is used by a display controller 14 to control the built-in display 12.

The external display device 3 comprises a second processing unit (CPU) 15, in which a display manager software is executed; i.e. the CPU 15 serves as a second display management device. The CPU 15 is adapted to process the transmitted communication data 10 and to generate imaging information from the communication data 10 by means of the display manager software in order to derive a graphical representation of domain-specific display objects on the external display 13 from the generated imaging information. In other words, the CPU 15 expands ("decompresses") the small amount if communication data 10 and generates medical objects with the same "look and feel" as on the built-in display 12 of the patient monitor 2. In other words, the rendering process of graphical objects is performed completely on this side of the communication link. The CPU 15 is connected to a display controller 16 to control the external display 13 using the imaging information generated. Again, all components of the external display device 3 are connected to a power supply 17.

If the patient monitor's CPU 8 receives new monitoring data from the sensor 11, new communication data 10 is generated by means of the CPU 8, but only in the event of a change in monitoring data. If the monitoring data does not change, e.g. the heart rate remains constant, no communication data 10 is generated and transmitted to the external display device 3. The amount of transmitted data can thus be limited to a minimum.

In a first embodiment of the invention, the display manager software executed in the CPU 15 of the external display device 3 is not identical to the display manager software executed in the CPU 8 of the patient monitor 2. In this case, the display manager software executed in the CPU 15 of the external display device 3 mainly comprises a graphic machine (rendering engine). This graphic machine is adapted to generate imaging information from the received communication data 10, which information can be used to control the object displayed on the external display 13 by means of the display controller 16 of the external display device 3 such that all objects are displayed in their correct size and the correct layout. Thus, the knowhow of rendering medical objects is implemented within this special graphic machine, based on data as used internally within the patient monitor 2. The main advantage of this embodiment of the invention is that it is not necessary to implement the complete functionality of the display manager software executed in the CPU 8 of the patient monitor 2 in the CPU 15 of the external display device 3, i.e. only little effort is necessary in order to implement the invention.

In another embodiment of the invention (not illustrated), the display manager software executed in the CPU 15 of the external display device 3 is identical to the display manager software executed in the CPU 8 of the patient monitor 2, i.e. the first and second display management devices are identical. This is preferably the case where a second patient monitor is used as the external display device. In this embodiment the cost of implementing the present invention is a minimum.

In summary, the present invention realizes a re-use of a known display management software of a patient monitor 2 in an external display device 3 in order to establish an external display 13 which operates in the same way as an internal, built-in display 12 of the patient monitor 2. The communication between the patient monitor 2 and the external display device 3 is realized such that a minimum amount of data is transmitted. To realize this kind of "thin" communication, only logical data necessary for deriving a graphical representation of domain-specific display objects on the external display 13 are transmitted. Preferably, only a cut-down version of the original display management software is used in the external display device 3 for graphically rendering the medical objects in accordance with the received logical data.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit, may fulfil the functions of several means recited in the claims. Any reference signs in the claims shall not be construed as limiting the claim concerned.

REFERENCE NUMERALS 1 patient-monitoring system
2 patient monitor
3 external display device
4 communication link
5 system interface
6 LAN interface
7 power supply
8 CPU
9 sensor
10 communication data
11 measurement interface
12 built-in display
13 external display
14 display controller
15 CPU
16 display controller
17 power supply

The invention claimed is:

1. A method of deriving a graphical representation of domain-specific display objects on an external display within a patient-monitoring system, comprising the steps of:
   processing monitoring data and generating communication data from the monitoring data with a first display management device, which is included in a patient monitor, wherein the communication data includes logical data from which is derived a graphical representation of domain specific display objects on the external display,
   transmitting the generated communication data to an external display device, which is connectable to the patient monitor, via a communication link,
   processing the transmitted communication data and generating imaging information from the communication data with a second display management device, which is included in the external display device, and
   deriving a graphical representation of domain-specific display objects on the external display from the generated imaging information, wherein the logical data from which the graphical representation of domain specific display objects is derived for display on the external display optimizes and changes a layout of objects within an available display screen surface of the external display.

2. The method as claimed in claim 1, wherein no communication data is transmitted to the external display device if the monitoring data does not change.

3. The method as claimed in claim 1, wherein graphical support data is included into the communication data.

4. The method as claimed in claim 1, wherein the second display management device utilizes the same display manager software as the first display management device.

5. The method as claimed in claim 1, further including:
generating first imaging information from the communication data with the first display management device which is displayed on a display of the patient monitor; and
generating second imaging information from the communication data with the second display management device which is displayed on a display of the external display.

6. The method as claimed in claim 5, wherein the communication data does not include monitoring data or imaging information.

7. A patient monitoring system, comprising:
a patient monitor which includes a first display management device configured to process monitoring data and generate communication data from the monitoring data, wherein the communication data includes logical data necessary for deriving a graphical representation of domain-specific display objects on an external display, and
an external display device, connectable to the patient monitor via a communication link that is configured to transmit the communication data, which external display device includes a second display management device configured to process the transmitted communication data and generate imaging information from the communication data so as to derive a graphical representation of domain-specific display objects on the external display from the generated imaging information,
wherein the logical data necessary for deriving a graphical representation of domain specific display objects on the external display optimizes a layout of objects within an available display screen surface of the external display;
wherein the external device displays a different layout of objects from the patient monitor.

8. The patient monitoring system as claimed in claim 7, wherein a second patient monitor serves as the external display device.

9. The patient monitoring system as claimed in claim 7, wherein first and second display management devices are identical.

10. The system as claimed in claim 7, wherein the first display management device includes:

a first display controller which generates first imaging information from the communication data, the first imaging information being displayed on the patient monitor; and
the second display management device includes:
a second display controller which generates second imaging information from the communication data, the second imaging information being displayed on the external display.

11. The system as claimed in claim 7, wherein the second display management device utilizes the same display manager software as the first display management device.

12. The system as claimed in claim 7, wherein the communication data does not include monitoring data or imaging information.

13. A patient monitoring system, the system comprising:
a patient monitor including:
a measurement interface configured to generate monitoring data from one or more sensors;
a first display management device configured to generate communication data from the monitoring data, the communication data including logical data which is processed internally within the first display management device to derive a first graphical representation of domain specific display objects;
a first display device configured to display the first graphical representation of domain specific display objects; and
a first communication device configured to transmit the communication data to an external display device;
the external display device including:
a second communication device configured to receive the communication data from the first communication device of the patient monitor;
a second display management device configured to derive a second graphical representation of domain specific display objects from the logical data within the communication data; and
a second display device configured to display the second graphical representation of domain specific display objects;
wherein the second graphical representation includes a different layout of objects from first graphical representation.

14. The system as claimed in claim 13, wherein the first and second display management devices are identical.

15. The system as claimed in claim 13, wherein the logical data optimizes a layout of objects within an available display screen surface of at least the first and second display devices.

16. The system as claimed in claim 13, wherein the communication data does not include monitoring data or imaging information.

* * * * *